United States Patent
Sugio et al.

(10) Patent No.: US 6,977,313 B2
(45) Date of Patent: Dec. 20, 2005

(54) PRODUCTION PROCESS OF 2,7-DIBROMOFLUORENONE

(75) Inventors: Youko Sugio, Tokyo (JP); Naoyuki Kitamura, Tokyo (JP); Hiroaki Mori, Tokyo (JP); Tetsuo Hachiya, Tokyo (JP)

(73) Assignee: JFE Chemical Corporation, Tokyo (JP)

( * ) Notice: Subject to any disclaimer, the term of this patent is extended or adjusted under 35 U.S.C. 154(b) by 0 days.

(21) Appl. No.: 10/667,304

(22) Filed: Sep. 23, 2003

(65) Prior Publication Data

US 2004/0059160 A1 Mar. 25, 2004

(30) Foreign Application Priority Data

Sep. 24, 2002 (JP) .............................. 2002-277338

(51) Int. Cl.$^7$ .............................................. C07C 45/00
(52) U.S. Cl. ...................................... 568/321; 568/330
(58) Field of Search ................................. 568/321, 330

(56) References Cited

U.S. PATENT DOCUMENTS

| | | | | |
|---|---|---|---|---|
| 4,009,151 A | * | 2/1977 | Pearson et al. | 526/284 |
| 5,288,915 A | * | 2/1994 | Walters | 568/323 |
| 6,344,585 B2 | | 2/2002 | Mori | 562/460 |

FOREIGN PATENT DOCUMENTS

| | | | | |
|---|---|---|---|---|
| JP | 6-211729 | | 8/1994 | |
| JP | 7082206 | * | 3/1995 | ........... C07C/45/36 |

OTHER PUBLICATIONS

Spinzak, Yair. Reactions of Active Methylene Compounds in Pyridine Solution. The Ionic Autoxidation of Fluorene and its Derivatives. J. Amer. Chem. Soc. 1958, (80) p 5449–5455.*

A. Novelli, "Derivados Azometinicos del Fluoreno", Aneles Asocn. Quim. Argentina, 25, 19927, pp. 187–209.

A. Novelli, "Azomethine Derivatives of Fluorene", Anales de la Asociacion Quimica Argentina, 25, (1927), pp. 187–209 w/English Abstract.

* cited by examiner

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

A process is provided for the production of 2,7-dibromofluorenone. According to the process, a 2,7-dibromofluorene-contianing raw material is oxidized with molecular oxygen in the presence of a phase transfer catalyst such as a quaternary ammonium salt in a heterogeneous, mixed solvent of an aqueous solution of a caustic alkali and a water-insoluble organic solvent. Crude crystals of 2,7-dibromofluorenone, which have been obtained by the oxidization, can be purified by recrystallization to recover 2,7-dibromofluorenone as crystals having a purity of at least 99 wt. %.

4 Claims, No Drawings

PRODUCTION PROCESS OF 2,7-DIBROMOFLUORENONE

FIELD OF THE INVENTION

This invention relates to a process for producing 2,7-dibromofluorenone by subjecting 2,7-dibromofluorene to liquid phase oxidation with a molecular-oxygen-containing gas, and especially, to a process which permits high yield production of 2,7-dibromofluorenone from 2,7-dibromofluorene as a raw material.

DESCRIPTION OF THE BACKGROUND 2,7-Dibromofluorenone is a substance useful as a raw material for agrichemicals, medicines, high functional polymers, dyes, pigments, and photosensitizers. Oxidation of 2,7-dibromofluorene is known to be able to produce 2,7-dibromofluorenone.

Conventionally-known processes for the production of 2,7-dibromofluorenone from 2,7-dibromofluorene include oxidation with a chemical such as chromic anhydride, nitric acid, potassium permanganate or potassium dichromate. Such chemical oxidation, however, involves problems in health and environment in addition to a problem in productivity, and therefore, is not suited for the industrial production of 2,7-dibromofluorenone (see JP 58-177955 A).

On the other hand, a process is known to produce 2,7-dibromofluorenone by reacting 2,7-dibromofluorene and p-dimethylaminonitrosobenzene in ethanol in the presence of metallic sodium or potassium cyanide as a catalyst (see N. Novelli, Anales asocn. quim. Argentina, 25, 187 (1927)). According to this process, a byproduct is reacted further in the presence of metallic sodium catalyst in a mixture of the raw material, 2,7-dibromofluorene, and ethanol to produce 2,7-dibromofluorenone. However, these catalysts are all costly and difficult in handling so that the above-mentioned process is not considered to be a practical process.

In other words, the above-described conventional processes are different from the process of the present invention which will hereinafter be described in detail, because the former processes are each different in the reaction system or the catalyst component from the latter process. From the standpoint of economy, the conventional processes are not fully satisfactory.

SUMMARY OF THE INVENTION

An object of the present invention is to provide an industrially-economical process for the production of 2,7-dibromofluorenone. Specifically, it is an object of the present invention to provide an oxidation process of 2,7-dibromofluorene, which can form 2,7-dibromofluorenone from 2,7-dibromofluorene at high conversion without byproducts such as high-molecular substances by using an economical catalyst having high handling ease. Another object of the present invention is to provide a process for producing 2,7-dibromofluorenone (crude 2,7-dibromofluorenone), which can recover high-purity 2,7-dibromofluorenone with high yield by an industrially-economical purification method, specifically, by recrystallization with an economical solvent.

The above-described objects can be achieved by the present invention to be described hereinafter. In one aspect of the present invention, there is thus provided a process for the production of 2,7-dibromofluorenone. The process includes oxidizing a 2,7-dibromofluorene-containing raw material with molecular oxygen in the presence of a phase transfer catalyst such as a quaternary ammonium salt in a heterogeneous, mixed solvent of an aqueous solution of a caustic alkali and a water-insoluble organic solvent. According to this process, 2,7-dibromofluorenone can be industrially produced with high yield, in a short time and at economical cost. Further, an aqueous alkaline solution which can be separated after the oxidation can be used repeatedly without applying any special treatment such as concentration. This leads to a further improvement in productivity and also to a reduction in the consumption of the phase transfer catalyst such as quaternary ammonium salt. Moreover, the use of the water-insoluble organic solvent makes it possible to complete separation of the organic solvent from water in a short time and then, to recover the organic solvent by distillation. These lead to a still further improvement in productivity.

In another aspect of the present invention, there is also provided a process for the production of 2,7-dibromofluorenone. According to the process, crude crystals of 2,7-dibromofluorenone, which have been obtained by the oxidization, are purified by recrystallization to recover 2,7-dibromofluorenone as crystals having a purity of at least 99 wt. %. According to this invention, 2,7-dibromofluorenone can be obtained by simple recrystallization from 2,7-dibromofluorenone produced by the above-described process of the present invention.

DETAILED DESCRIPTION OF THE PREFERRED EMBODIMENTS

The present invention will next be described in further detail on the basis of preferred embodiments. No particular limitation is imposed on the 2,7-dibromofluorene-containing raw material for use as a raw material in the present invention. However, a high-purity raw material is desired, and one having a 2,7-dibromofluorene content of 70 wt. % or higher, preferably 90 wt. % or higher can be used desirably.

Examples of the phase transfer catalyst for use in the present invention can include quaternary ammonium salts such as tetramethylammonium chloride, tetraethylammonium bromide, tetrabutylammonium bromide, tetrabutylammonium hydroxide and tetraethylammonium hydroxide; and phosphonium salts such as methyltriphenylphosphonium bromide and tetraphenylphosphonium bromide.

The phase transfer catalyst such as a quaternary ammonium salt acts as a catalyst in the oxidation of 2,7-dibromofluorene. It can be used in a proportion of from 0.1 to 20 g, preferably from 1 to 10 g per mole of 2,7-dibromofluorene used as a raw material. No particular limitation is imposed on the form of use of the phase transfer catalyst such as a quaternary ammonium salt. If necessary from the standpoint of handling convenience, it may be used, for example, in the form of an aqueous solution or an alcohol solution.

It is necessary to use an aqueous solution of a caustic alkali along with the phase transfer catalyst such as a quaternary ammonium salt and to oxidize 2,7-dibromofluorene in the presence of the phase transfer catalyst such as a quaternary ammonium salt and the aqueous solution of the caustic alkali. Illustrative of the aqueous solution of the caustic alkali for use in the present invention are aqueous solutions of alkali metals or alkaline earth metals such as sodium hydroxide, potassium hydroxide and calcium hydroxide. The aqueous solution of the caustic alkali may preferably be used as an aqueous solution of high concentration, specifically as a 30–50 wt. % aqueous solution, with a 35–48 wt. % aqueous solution being desired. The aqueous solution of the caustic alkali maybe used in a proportion of from 0.1 to 100 equivalents, preferably from 1 to 50 equivalents in terms of the caustic alkali per mole of 2,7-dibromofluorene. In this aqueous solution of the caustic alkali, the above-described catalyst is dissolved, and after completion of the oxidation, the aqueous solution can be separated from the phase of the water-insoluble organic solvent and can be reused as the catalyst-containing aqueous solution of the caustic alkali, as will be described subsequently herein.

Water-insoluble organic solvents usable in the present invention can include, but are not limited to, toluene, ethylbenzene, aromatic amines, chloroform, and high boiling point, aromatic hydrocarbon solvents known under trade names such as "SWASOL 1500" (product of Maruzen Petrochemical Co., Ltd.) and "Cactus Solvent P-150" (product of Nikko Petrochemicals Co., Ltd.). These solvents are insoluble in water, but are preferred for their ability to dissolve 2,7-dibromofluorene and their economy upon recovering them from the reaction mixture. From the standpoint of work efficiency, toluene, ethylbenzene and the like are preferred. The solvent may be used preferably in a proportion of from 500 to 5,000 mL, more preferably in a proportion of from 1,000 to 4,000 mL per mole of 2,7-dibromofluorene.

The liquid phase oxidation of 2,7-dibromofluorene with the molecular-oxygen-containing gas can be carried out by causing the molecular-oxygen-containing gas to flow into a reaction system which contains, for example, 2,7-dibromofluorene, the phase transfer catalyst, the water-insoluble organic solvent and the like. The flow rate of the molecular-oxygen-containing gas may generally be from 500 to 6,000 NmL/min, preferably from 1,000 to 5,000 NmL/min per mole of 2,7-dibromofluorene employed as a raw material, although it differs depending on the catalyst, the temperature of a gas, the reaction temperature and the like. The unit "NmL/min" means the volume of a gas per unit time (min) as caused to flow under conditions of 25° C. and 1 atm. As an alternative, the molecular-oxygen-containing gas can be charged along with 2,7-dibromofluorene, the phase transfer catalyst, the water-insoluble organic solvent and the like into a batch autoclave, and can then be reacted. Incidentally, no particular limitation is imposed on the molecular-oxygen-containing gas for use in the present invention insofar as it contains oxygen molecules. Illustrative are air, oxygen gas, and their mixed gases with inert gases such as argon gas and nitrogen gas.

The reaction temperature of the liquid phase oxidation of 2,7-dibromofluorene with the molecular-oxygen-containing gas may be from 35 to 100° C., with 40 to 70° C. being preferred. No particular limitation is imposed on the reaction pressure, and the reaction can proceed sufficiently even under environmental pressure.

2,7-Dibromofluorenone can be recovered, for example, by optionally washing the reaction mixture, which has been obtained by the liquid phase oxidation of 2,7-dibromofluorene and contains 2,7-dibromofluorenone, with an acid or water as needed and evaporating the used water-insoluble organic solvent. It is preferred to further recrystallize the resultant 2,7-dibromofluorenone (crude 2,7-dibromofluorenone) from an aromatic hydrocarbon, amide, ketone, ester or the like for its recovery in a purified form. Preferred examples of such a recrystallization solvent can include toluene, N,N'-dimethylformamide, acetone, tetrahydrofuran, and ethyl acetate. These solvents can be used either singly or in combination.

The phase transfer catalyst can be eliminated into a water phase when the reaction solvent is washed with an acid or water, and can also be eliminated into a recrystallization solvent upon recrystallization. The phase transfer catalyst can also be eliminated by subjecting it to adsorptive separation with a general solid acid or ion-exchange resin.

EXAMPLES

The present invention will hereinafter be described in further detail based on Examples. It is, however, to be noted that the present invention is not limited only to such Examples. In the following Examples, each designation of "%" means "wet. %" unless otherwise specifically indicated.

Example 1

Into a three-necked, 300-mL flask equipped with a stirrer, a molecular-oxygen-containing gas (air) inlet tube and a gas outlet tube (fitted with a condenser), 2,7-dibromofluorene (9.29 g, 0.029 mol) was charged, followed by its dissolution with toluene (100 g). Subsequent to addition of tetraammonium bromide (0.24 g) and a 48% aqueous solution of sodium hydroxide (2.66 g), the resulting mixture was vigorously stirred at 60° C. for 2 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (8.31 g).

Purity: 99.3%, yield: 90.2%, melting point: 206° C. (gas chromatography: As a column, "DB-5" was used).

Example 2

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with "Cactus Solvent P-150" (product of Nikko Petrochemicals Co., Ltd.; 100 g). Subsequent to addition of tetraammonium bromide (0.24 g) and a 48% aqueous solution of sodium hydroxide (2.66 g), the resulting mixture was vigorously stirred at 60° C. for 2 hours while introducing air at a flow rate of 0.1 L/min. After completion of the stirring, the reaction mixture was allowed to stand, and the resulting "Cactus Solvent P-150" layer was collected. The "Cactus Solvent P-150" layer was then subjected to acid washing, followed by water washing until its pH arose to 7. "Cactus Solvent P-150" was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (7.67 g).

Purity: 99.1%, yield: 83.2%, melting point: 206° C. (gas chromatography: As a column, "DB-5" was used).

Example 3

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium chloride (0.21 g) and a 48% aqueous solution of sodium hydroxide (2.66 g), the resulting mixture was vigorously stirred at 60° C. for 2 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (8.06 g).

Purity: 99.1%, yield: 87.4%, melting point: 206° C. (gas chromatography: As a column, "DB-5" was used).

Example 4

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of a 25% aqueous solution of tetraammonium hydroxide (0.77 g) and a 48% aqueous solution of sodium hydroxide (2.66 g), the resulting mixture was vigorously stirred at 60° C. for 3 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (8.26 g).

Purity: 99.1%, yield: 89.6%, melting point: 206° C. (gas chromatography: As a column, "DB-5" was used).

Example 5

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium bromide (0.24 g) and a 48% aqueous solution of sodium hydroxide (2.66 g), the resulting mixture was vigorously stirred at 60° C. for 2 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from a 1:1 (by weight ratio) mixed solvent of acetone and toluene (150 g) to afford 2,7-dibromofluorenone as yellow crystals (7.14 g).

Purity: 99.2%, yield: 77.5%, melting point: 206° C. (gas chromatography: As a column, "DB-5" was used).

Example 6

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium bromide (0.24 g) and a 48% aqueous solution of sodium hydroxide (2.66 g), the resulting mixture was vigorously stirred at 60° C. for 2 hours while introducing air at a flow rate of 0.2 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (7.86 g).

Purity: 99.0%, yield: 85.3%, melting point: 206° C. (gas chromatography: As a column, "DB-5" was used).

Example 7

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium bromide (0.24 g) and a 35% aqueous solution of sodium hydroxide (2.66 g), the resulting mixture was vigorously stirred at 60° C. for 2 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (7.79 g).

Purity: 99.5%, yield: 84.5%, melting point: 206° C. (gas chromatography: As a column, "DB-5" was used).

Example 8

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium bromide (0.24 g) and a 48% aqueous solution of sodium hydroxide (2.66 g), the resulting mixture was vigorously stirred at 40° C. for 5 hours while introducing air at a flow rate of 0.1 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (7.83 g).

Purity: 99.2%, yield: 84.9%, melting point: 206° C. (gas chromatography: As a column, "DB-5" was used).

Example 9

Into a three-necked, 300-mL flask equipped with a stirrer, a molecular-oxygen-containing gas (air) inlet tube and a gas outlet tube (fitted with a condenser), 2,7-dibromofluorene (9.30 g, 0.029 mol) was charged, followed by its dissolution with toluene (100 g). Subsequent to addition of tetraammonium bromide (0.08 g) and a 48% aqueous solution of sodium hydroxide (2.66 g), the resulting mixture was vigorously stirred at 60° C. for 6 hours while introducing air at a flow rate of 0.2 L/min. After completion of the stirring, the reaction mixture was allowed to stand, and the resulting toluene layer was collected. The toluene layer was then subjected to acid washing, followed by water washing until its pH arose to 7. Toluene was then distilled off to recover crude crystals of 2,7-dibromofluorenone. The content of 2,7-dibromofluorene in the crude crystals at that time was 0%. Those crude crystals were recrystallized from N,N'-dimethylformamide (15 g) to afford 2,7-dibromofluorenone as yellow crystals (7.91 g).

Purity: 99.0%, yield: 85.8%, melting point: 206° C. (gas chromatography: As a column, "DB-5" was used).

This application claims the priority of Japanese Patent Application 2002-277338 filed Sep. 24, 2002, which is incorporated herein by reference.

What is claimed is:

1. A process for the production of 2,7-dibromofluorenone, comprising oxidizing a 2,7-dibromofluorene-containing raw material with molecular oxygen in the presence of a phase transfer catalyst in a heterogeneous, mixed solvent of an aqueous solution of a caustic alkali and a water-insoluble organic solvent.

2. A process according to claim 1, further comprising purifying crude crystals of 2,7-dibromofluorenone, which have been obtained by said oxidization, by recrystallization to recover 2,7-dibromofluorenone as crystals having a purity of at least 99 wt. %.

3. A process according to claim 1, wherein said phase transfer catalyst is a quaternary ammonium salt.

4. A process according to claim 3, further comprising purifying crude crystals of 2,7-dibromofluorenone, which have been obtained by said oxidization, by recrystallization to recover 2,7-dibromofluorenone as crystals having a purity of at least 99 wt. %.

* * * * *